(12) United States Patent
Peters et al.

(10) Patent No.: US 7,347,811 B2
(45) Date of Patent: Mar. 25, 2008

(54) HEART ASSIST DEVICE UTILISING AORTIC DEFORMATION

(75) Inventors: William Suttle Peters, Auckland (NZ); Scott Hugh Miller, Manly (AU); Peter Andrew Watterson, West Ryde (AU)

(73) Assignee: Sunshine Heart Company Pty Ltd., New South Wales (AU)

( * ) Notice: Subject to any disclaimer, the term of this patent is extended or adjusted under 35 U.S.C. 154(b) by 408 days.

(21) Appl. No.: 10/702,834

(22) Filed: Nov. 5, 2003

(65) Prior Publication Data

US 2004/0097783 A1    May 20, 2004

(30) Foreign Application Priority Data

Nov. 15, 2002   (AU)   ................ 2002952691

(51) Int. Cl.
*A61N 1/362*   (2006.01)

(52) U.S. Cl. .......................................... 600/18

(58) Field of Classification Search ............. 600/16–18
See application file for complete search history.

(56) References Cited

U.S. PATENT DOCUMENTS

| | | | |
|---|---|---|---|
| 4,014,318 A | 3/1977 | Dockum et al. |
| 4,176,411 A | 12/1979 | Runge |
| 4,195,623 A | 4/1980 | Zeff et al. |
| 4,304,225 A | 12/1981 | Freeman |
| 4,583,523 A | 4/1986 | Kleinke et al. |
| 4,630,597 A | 12/1986 | Kantrowitz et al. |
| 4,771,765 A | 9/1988 | Choy et al. |
| 4,809,676 A | 3/1989 | Freeman |
| 4,813,952 A | 3/1989 | Khalafalla |
| 4,979,936 A | 12/1990 | Stephenson et al. |
| 5,205,810 A | 4/1993 | Guiraudon et al. |
| 5,222,980 A | 6/1993 | Gealow |
| 5,267,940 A | 12/1993 | Moulder |
| 5,273,518 A | 12/1993 | Lee |
| 5,372,573 A | 12/1994 | Habib |
| 5,429,584 A | 7/1995 | Chiu |
| 5,647,380 A | 7/1997 | Campbell et al. |
| 6,030,336 A | 2/2000 | Franchi |
| 6,045,496 A | 4/2000 | Pacella et al. |
| 6,471,633 B1 | 10/2002 | Freed |
| 6,808,484 B1 | 10/2004 | Peters et al. |

FOREIGN PATENT DOCUMENTS

| | | |
|---|---|---|
| EP | 0216042 A1 | 4/1987 |
| EP | 0216042 B1 | 6/1991 |
| WO | WO 92/08500 | 5/1992 |
| WO | WO 99/04833 | 2/1999 |
| WO | WO 01/13974 | 3/2001 |

OTHER PUBLICATIONS

WO 00/76288, Peters et al.*

* cited by examiner

*Primary Examiner*—Scott M. Getzow
(74) *Attorney, Agent, or Firm*—Orrick, Herrington & Sutcliffe, LLP

(57) ABSTRACT

The present invention relates to providing counter-pulsation heart assist by deforming the aorta. In a preferred embodiment, the deformation pressure is applied by cyclically, preferably in synchrony with the diastolic period of the heart. The deformation pressure may be applied to the outer wall of the aorta or to a patch covering a resected opening in the wall of the aorta.

44 Claims, 7 Drawing Sheets

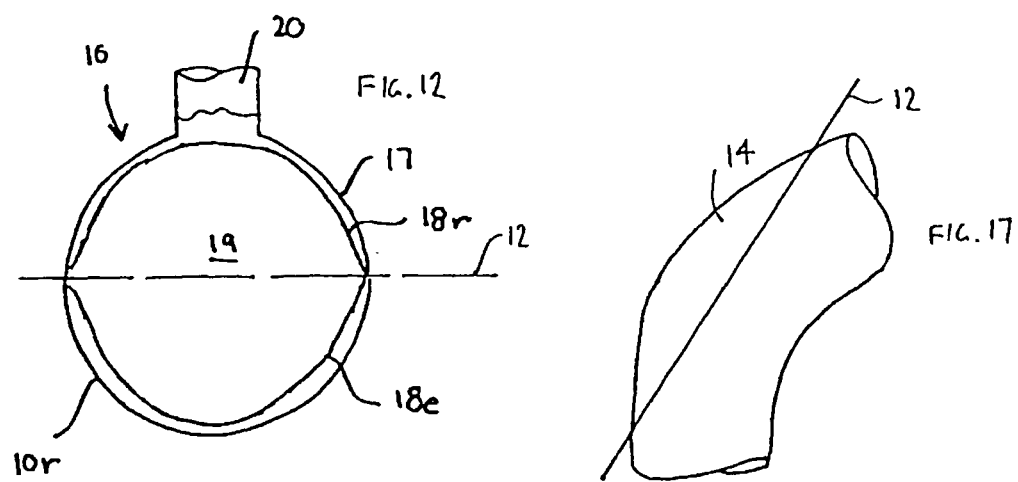
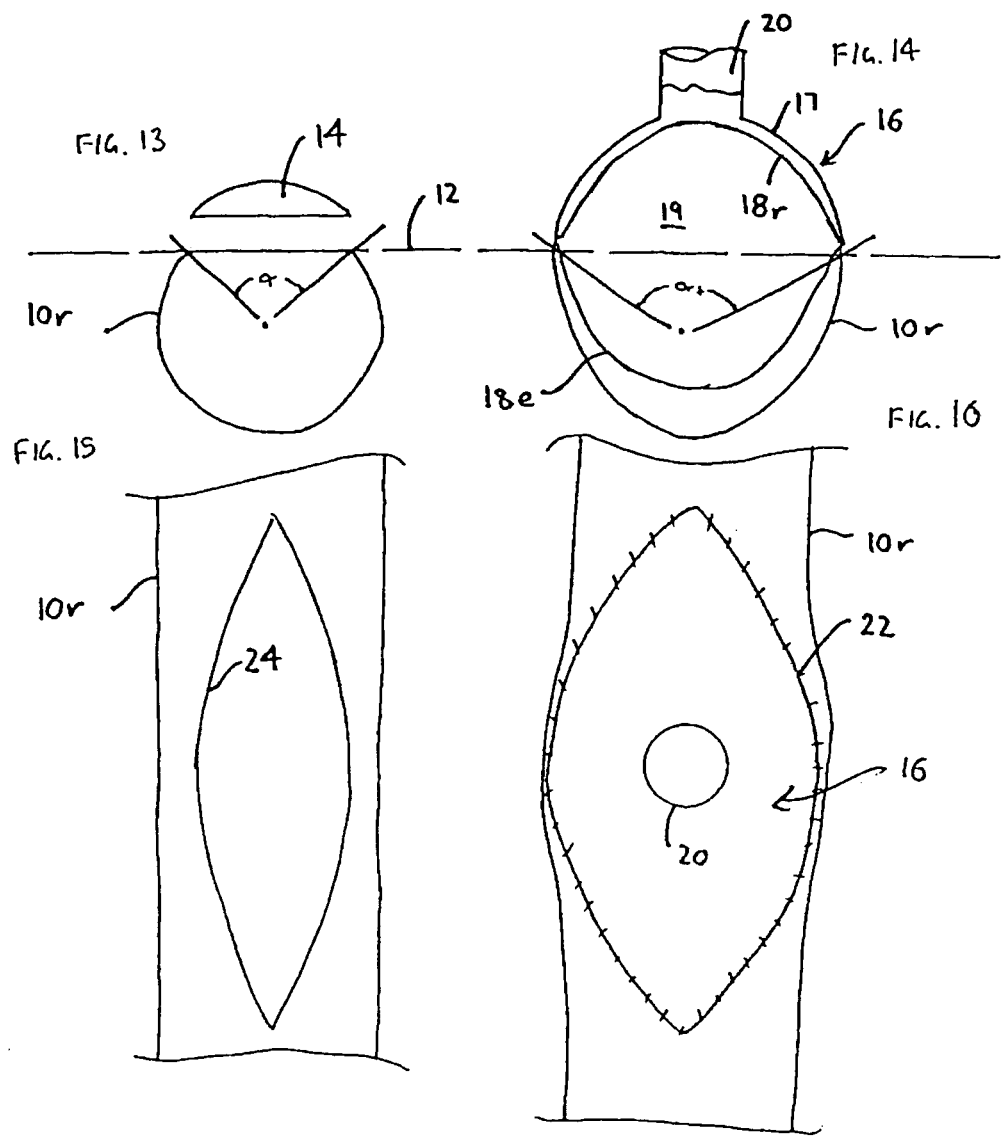

HEART ASSIST DEVICE UTILISING AORTIC DEFORMATION

RELATED INFORMATION

This application claims priority to Australian Provisional Application No. 2002952691 filed on Nov. 15, 2002. The priority of this prior application is expressly claimed, and the disclosure of the provisional application is hereby incorporated by reference in its entirety.

FIELD OF THE INVENTION

The present invention relates generally to counterpulsation heart assist devices, systems and methods and, more particularly, to heart assist devices utilising aortic deformation and/or aortic resection.

BACKGROUND OF THE INVENTION

The concept of providing counter-pulsation support for the failing heart has been known since the pioneering work of Kantrowitz. Counter-pulsation causes displacement of a volume of a patient's blood in the patient's aorta while the patient's heart is dilating in diastole and after the aortic valve has closed. This assists to move blood around the patient's peripheral vasculature as well as into the coronary arteries. The timed volume displacement in the aorta on the blood within the aorta just in advance of systolic ejection of blood from the heart reduces the afterload on the heart, by causing a transient low pressure above the aortic valve.

It is known from the use of counter-pulsation in Intra-Aortic Blood Pumps (IABPs) that counter-pulsation can provide short term support for the failing heart. These devices require a balloon to be inserted percutaneously into the descending aorta. The balloon is inflated and deflated in counter-pulsation with the heart by the transmission of a gas, usually helium, between the balloon and a bedside console. These devices suffer from the problem that there is a high risk of thrombo-embolism if the balloon remains in the vasculature for a prolonged period, which can lead to ischemic leg complications.

There have been a number of attempts to provide counter-pulsation support for the failing heart by applying counter-pulsation pressure to the outside of the aorta. These proposals are contained in the following patent specifications:

| PCT | 99/04833 |
|---|---|
| U.S. Pat. No. | 4,014,318 |
| U.S. Pat. No. | 4,583,523 |
| U.S. Pat. No. | 4,979,936 |
| U.S. Pat. No. | 6,030,336 |
| U.S. Pat. No. | 6,045,496 |

A similar arrangement is described by Furman, New York Journal of Medicine, Aug. 1, 1970, pp 1964-1969. In all of these arrangements means are provided to surround, or at least substantially surround, the aorta and to apply a squeezing pressure substantially uniformly around the circumference of the aorta. The present inventors have found that there are substantial advantages if the counter-pulsation pressure is applied to only a part of the circumference of the aorta.

It is also known to resect a part of the aorta for the purpose of inserting a patch or other graft into the aorta and to cause such patch or graft to counterpulsate. Such a system is described in the following patent specifications:

| PCT | 01/13974 |
|---|---|
| U.S. Pat. No. | 4,630,597 |

The device described in these specifications is for insertion into the descending aorta which is straight. There is no suggestion of how to deal with the more complex issues that arise in placing the device into the ascending aorta which is curved along its length.

OBJECT OF THE INVENTION

It would be desirable to have a heart assist device, which may or may not be blood contacting, that could provide assistance to the heart function with reduced risk to the patient and/or of device malfunction than prior art devices.

SUMMARY OF THE INVENTION

In one aspect, the present invention provides a device for assisting the functioning of the heart of a patient, the device including:

an aortic compression means adapted, when actuated, to compress an aorta; and motive means to periodically actuate, and de-actuate, the aortic compression means in counter-pulsation with the patient's heart rhythm, wherein the aortic compression means is adapted to compress only a portion of the circumference of the aorta.

Preferably, the aortic compression means is adapted to compress less than half of the circumference of the aorta.

In one form, the aortic compression means is a mechanical device driven, upon actuation, into compressive contact with the exterior of the aorta. In another form, the aortic compression means includes a flexible membrane, which may be elastic or inelastic, driven, upon inflation, into compressive contact with the exterior of the aorta.

The aortic compression means is preferably adapted to compress only a portion of the circumference of the ascending aorta, most preferably only the radially outer side of the ascending aorta.

In a second aspect, the present invention provides, in a heart assist device of the type which induces counter-pulsation of an artery in the vasculature of a patient, the improvement comprising the application of a counter-pulsation pressure to the exterior of the artery such that the artery is caused to flex along a continuous line which increases in length as the counterpulsation pressure applied to the artery increases.

The line preferably has the shape of a conic section.

In a third aspect, the present invention provides, in a heart assist device of the type which induces counterpulsation of an artery in the vasculature of a patient, the improvement comprising the application of a counterpulsation pressure to the exterior of the artery such that the artery is caused to compress substantially without stretching or bunching.

In a fourth aspect, the present invention provides, in a heart assist device which includes aorta deformation means to apply a counter-pulsation pressure to the ascending aorta of a patient, characterised in that the aorta deformation means applies a deforming force to the outside of the radially outer side of the curvature in the ascending aorta and that the aorta deformation means induces in the aorta a smoothly curved ovate depression as it moves to a position of maximum deformation of the aorta.

In a fifth aspect, the present invention provides, in a heart assist device which includes aorta deformation means to apply a counter-pulsation pressure to the descending aorta of a patient, characterised in that the aorta deformation means applies a deforming force to the outside of the descending aorta and that the aorta deformation means induces in the aorta a smoothly curved circular depression as it moves to a position of maximum deformation of the aorta.

In a sixth aspect, the present invention provides, in a heart assist device including artery deformation means adapted to periodically apply a deforming force to a curved artery in a direction substantially normal to a tangent to the radially outer surface of the longitudinal curve in the artery, the deforming force being such that the artery is progressively deformed along a line which lies in a plane running through the artery, the plane moving radially inwardly through the artery as the deformation increases.

In a seventh aspect, the present invention provides, in a counter-pulsation type heart assist device adapted for insertion into the wall of the ascending aorta of a patient, the device including an inflatable balloon extending around less than one half of the circumference of the aorta and means to inflate the balloon in counter-pulsation with the heart of a patient into which the device has been inserted, the balloon having a substantially inelastic outer layer and an inner layer with a shape which is, when the balloon is deflated, smoothly curved and facing directly inwardly into the lumen of the ascending aorta of the patient into which the device has been inserted. Alternatively the device may be applied to the outside of the wall of the aorta.

In an eighth aspect, the present invention provides, in a heart assist device adapted to apply a counter-pulsation force to a patch inserted into at least the radially outer arc of the ascending aorta the force being applied to the radially outer arc of the aorta to cause the wall or the patch to invaginate, the device being characterised in that it includes deformation means for the application of the pressure to the wall or patch which deformation means has, when the wall or patch is fully invaginated, a shape which is substantially a mirror image of the section of the wall or patch which has been invaginated before it was so invaginated. Alternatively the device may be applied to the outside of the wall of the aorta.

The above embodiment is designed to apply a compressive force to the artery so as to cause the blood therein to be displaced while causing the minimum trauma to the vessel. In preferred embodiments of the invention the compression of the ascending aorta is induced in a way which reduces the enclosed volume of the aorta while not unduly stretching or bunching the wall of the aorta.

The deformation of the artery may be induced by a balloon or by a rigid object. In either case the object inducing the deformation shall be so shaped that the desired form of deformation of the artery is achieved. In the case of a balloon, the balloon should be so shaped that as it is inflated it will take on a shape similar to that which is desired to be achieved in the artery. It must also be so placed on the artery that the desired smoothly flexing and smoothly shaped deformation is achieved. In the case of a rigid object the object should initially be of an appropriate shape to induce the desired deformation of the artery as it is advanced towards the artery either along a linear path or an arcuate one. Preferably, the deforming object will be moved into the artery in a direction which is radial of the artery and either at right angles to its axis, if it is straight, or at right angles to a tangent to the radially outer side of the artery, if it is curved.

Preferably, the deformation of the vessel does not extend around more than 180 degrees of the circumference of the vessel, more preferably no more than 160 degrees and even more preferably not more than 140 degrees and most preferably between 100 and 140 degrees. The cuff or balloon may extend further around the aorta than the preferred amount, however, the active deformation of the aorta preferably only extends around an arc of the aorta within the above limits. The desire of this design preference is to avoid the inside surface of the deformed vessel touching the inside surface of the vessel diametrically opposite the deformation.

In preferred embodiments the deformational force will be applied directly to the arterial wall. However, if desired a layer of any suitable material may be placed between the deformational member and the wall. In an alternative embodiment of the invention a section of the arterial wall may be resected and a patch applied which substantially replicates the shape of the native artery and the deformational force applied to the outside surface of that patch. In this embodiment of the invention the patch is applied to the radially outer arc of the ascending aorta and preferably has a shape similar to the section of the ascending aorta which has been removed.

The heart assist device of the present invention allows, at least in preferred embodiments, partial unloading of the heart and augmenting of the cardiac output of the heart.

After use, if the heart has recovered, the device can be left in situ, in an inactive state, until needed again. The device can also be used to administer on-demand, spaced-apart sessions of counterpulsation for treatment or relief from chronic myocardial ischemia and/or heart failure.

In a preferred form of the invention, the device is adapted for attachment to the ascending aorta. An upper mid-line sternotomy provides surgical access to the ascending aorta. Alternatively, a thoracotomy may be used to place the device on the descending aorta.

The motive means referred to above can be any means that is capable of cyclically introducing fluid, and withdrawing fluid, from an inflatable bladder, balloon or cuff. The motive means can include or be associated with means for detecting speed and completeness of the filling and emptying, and for monitoring the delivered fluid pressure. The motive means can also act to record the ECG, having electrodes positioned on the housing or as separate wires attached to body tissues.

In a further aspect, the present invention provides a method for improving cardiac performance in a subject, the method including the steps of:

implanting a device in accordance with any one of the preceding aspects of the invention fully within the thoracic cavity of a subject;

actuating the motive means to periodically introduce the fluid into the space in synchrony with the diastolic period to reduce the interior volume of the aorta; and alternating the period of actuation with periods of deactivation of the motive means to periodically withdraw the fluid from the space in synchrony with the commencement of the systolic period, thereby allowing the portion of the aorta adjacent the device to return to normal interior volume.

The method may include the step of resecting a portion of the ascending aorta in the shape of a toroidal truncate and sealingly attaching the periphery of the device to the periphery of the opening aorta.

In another aspect, the present invention provides a device for assisting the functioning of the heart of a patient, the device including:

a patch device sealingly attachable to the ascending aorta;

a flexible membrane sealingly attached to at least part of the interior of the patch device and defining an inflatable space adjacent the interior of the patch device; and motive means to periodically introduce into, and withdraw from, the space a fluid, in counter-pulsation with the patient's heart rhythm.

The patch device is preferably attachable to the radially outer side of the ascending aorta. In one form, the patch device is attachable to the periphery of an opening in the ascending aorta formed by resecting a portion of the aorta. The membrane has a shape substantially replicating that of the interior surface of the resected portion of the aorta. The flexible membrane preferably also substantially replicates the shape of the interior of the patch device when the fluid is withdrawn from the space. It is believed that this design feature will reduce the incidence of thrombo-embolism by presenting, when deflated, a blood flow path without regions that would cause sluggish blood flow. The patch device is preferably in the shape of a truncated portion of a torus. The aorta is preferably resected along a line on the radially outer side, or passing through, the diameter of the mid point cross section of the aorta. The membrane, when the fluid is introduced into the space, is preferably expanded towards, but not abutting, the adjacent interior wall of the aorta.

In another form, the patch device is attachable to the ends of the aorta formed by removing a length of the aorta. The patch device preferably includes a truncated substantially toroidal portion with an externally facing hump that forms the inflatable space. The membrane is preferably attached to the patch device about the periphery of the hump. The surface of the membrane remote the space preferably has a shape, when the fluid is withdrawn from the space, substantially replicating that of the interior surface of the removed portion of the aorta. The flexible membrane preferably also substantially replicates the shape of the interior of the hump when the fluid is withdrawn from the space. The hump is preferably disposed external to a line on the radially outer side, or passing through, the diameter of the mid point cross section of the aorta. The membrane, when the fluid is introduced into the space, is preferably expanded close to, but not abutting, the adjacent interior wall of the aorta.

BRIEF DESCRIPTION OF THE DRAWINGS

Preferred embodiments of the invention will now be described, by way of examples only, with reference to the accompanying drawings in which:

FIG. 12 is a schematic cross sectional end view of the aorta and device shown in FIG. 11;

FIG. 13 is a schematic cross sectional view of an aorta of reduced size with a resected portion;

FIG. 14 is a cross sectional end view of the aorta of FIGS. 13 and 15 after surgical attachment of a further embodiment of device for assisting in the functioning of the heart;

FIG. 15 is a schematic front view of the resected aorta shown in FIG. 13;

FIG. 16 is a schematic front view of the aorta and device shown in FIG. 15;

FIG. 17 is a schematic side view of an ascending aorta showing an alternatively positioned resection line;

DETAILED DESCRIPTION OF THE PREFERRED EMBODIMENTS

Figure 1:
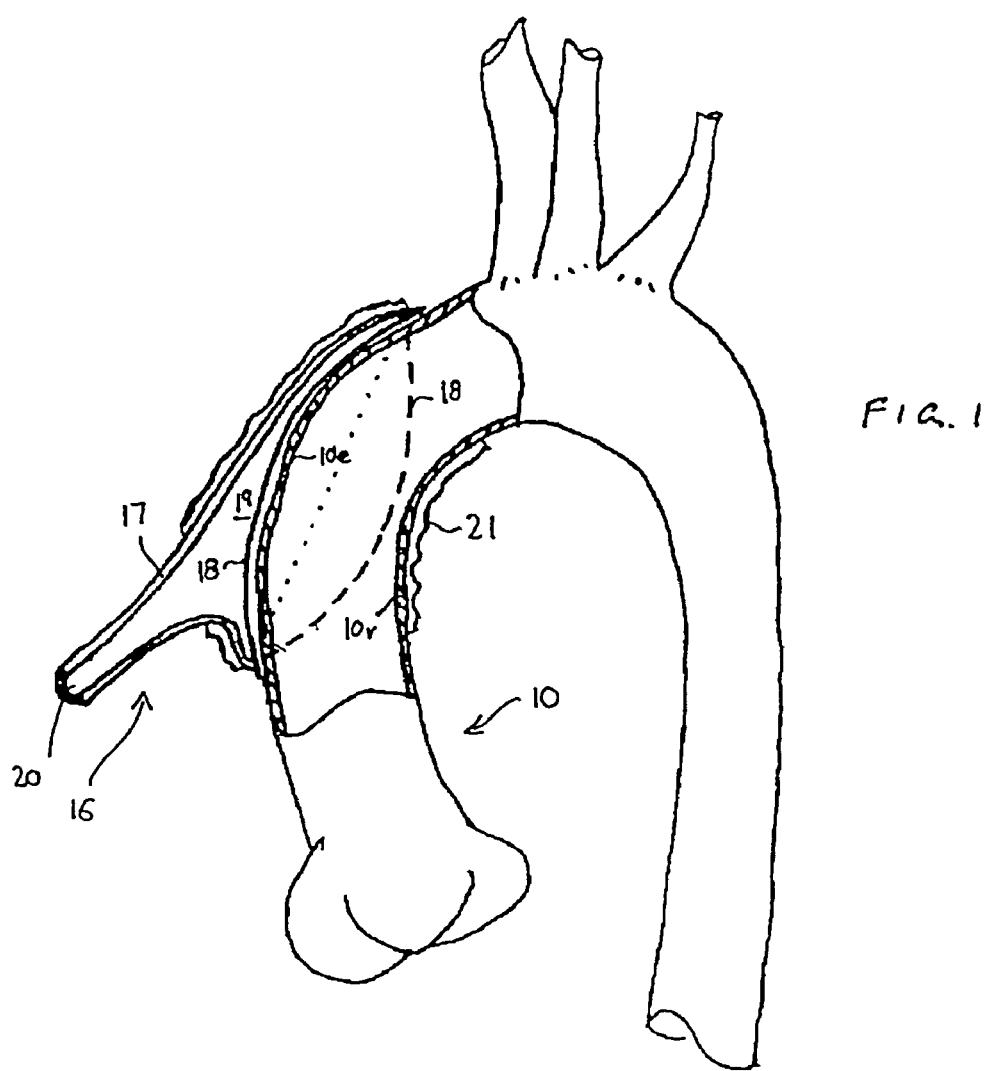
FIG. 1 is a cross sectional ventral view of the aorta of a patient with a first embodiment of a device for assisting the functioning of a heart.
Figure 2:
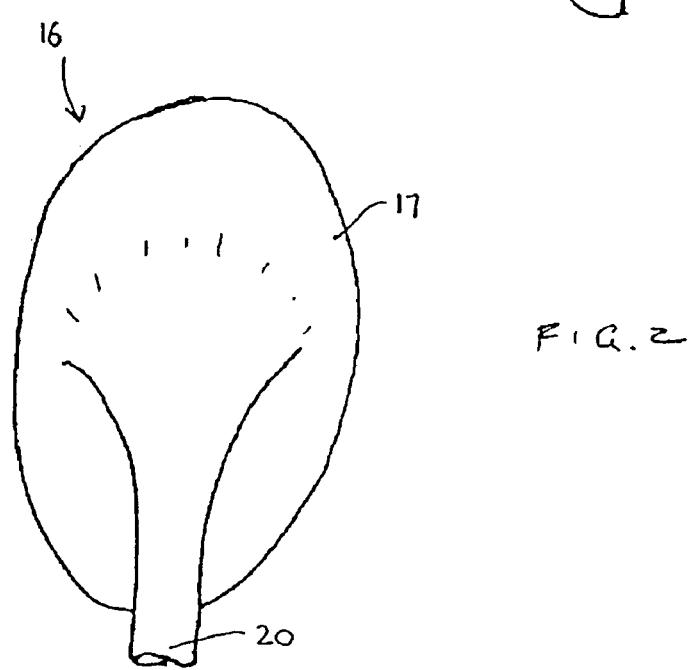
FIG. 2 is a schematic lateral view of the device shown in FIG. 1.
Figure 3:
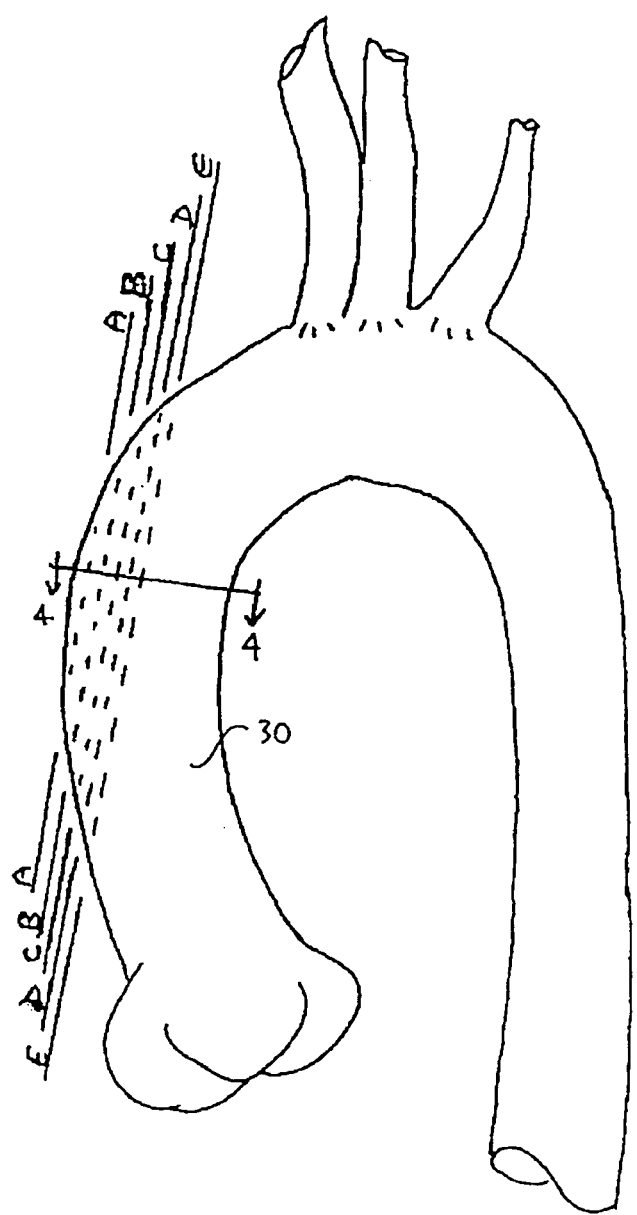
FIG. 3 is a ventral view of the aorta of a patient showing a series of planes through the aorta in which lines of flexure of the aortic wall will lie during application of a deforming force to the aorta.
Figure 4:
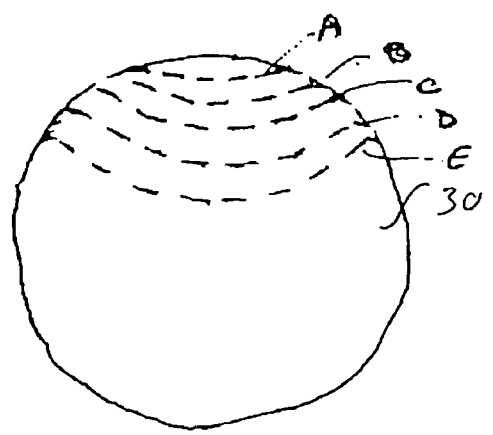
FIG. 4 is cross sectional view along line 4-4 through the aorta of FIG. 3 showing a sequence of shapes assumed by the aortic wall as it is deformed.

FIG. 1 is a schematic side view of an ascending aorta 10 and a heart assist device 16 in accordance with an embodiment of the invention. The device 16 has a relatively inelastic, preferably plastic, shell 17 and a flexible membrane 18 sealingly attached to the periphery of the shell 17. The membrane 18 defines an inflatable space 19 between it and the interior of the shell 17. The shell 17 also has an inlet/outlet port 20 which is adapted for connection to a motive means that can periodically introduce, and withdraw, a fluid (eg. a gas such as helium or a liquid such as a saline solution or an oil) to and from the space 19 in counter-pulsation with the patient's heart rhythm. The membrane 18 has a shape which is, when deflated, smoothly curved and facing directly inwardly towards the lumen of the ascending aorta 10.

A relatively inelastic wrap 21 is used to hold the device 16 in the position shown on the radially outer side of the ascending aorta 10.

The solid line 18 illustrates the position of the membrane 18 relative to the shell 17 when fluid has been withdrawn from the space 19 and the membrane 18 has been retracted. In this position the radially outer external side wall 10e of the aorta 10 is in its normal or deflated position allowing maximum blood flow there through.

The phantom line 18 illustrates the position of the membrane 18 relative to the shell 17 after fluid has been introduced into the space 19 and the membrane 18 has been expanded. When the membrane 18 is expanded in this way, the aorta external wall 10e is compressed and inwardly deformed until it is close to, but not abutting, the opposite interior wall of the aorta 10r.

The membrane 18 is sized and positioned to compress only a portion of the circumference of the radially outer side of the ascending aorta 10. More particularly, the membrane 18 compresses only about 140 degrees of the circumference of the aorta 10.

FIGS. 3 to 6 show, in various orientations and views, the shape the external wall 10e of the ascending aorta 10 assumes from initial deformation (line A) through to maximum deformation (line E). The lines A to E show the exterior of the aorta 10 flexing along a continuous line, that preferably has the shape of a conic section, which increases in length as the counter pulsation pressure applied to the artery increases. An advantage of flexing the aorta in this manner is that it is caused to compress substantially without stretching, which reduces the likelihood of damage. Also the line of flexure is constantly moving so that one line of the aorta 10 is not being constantly exposed to flexural movement. Put another way, the exterior of the aorta is deformed to induce a smoothly curved ovate depression as it moves towards a position of maximum deformation (line E) of the aorta 10. In an alternative embodiment, a smoothly curved circular depression can be formed in the aorta.

The lines A to E also show how the artery is progressively deformed along a line which lies in a plane running through the artery 10, that plane moving radially inwardly through the artery as the deformation increases.

The deformation described above can be caused to occur in many other different ways. For example, in another embodiment, deformation can be caused by a patch device inserted into the radially outer arc of the ascending aorta. In such an embodiment, the device includes a means for applying pressure to the wall or patch which, when the wall or patch is fully invaginated, forms a shape which is a mirror image of the section of the wall or patch which as been invaginated before it was so invaginated.

Another embodiment of a device for assisting the functioning of a heart according to the present invention will now be described in relation to FIGS. 7 to 12. Like reference numerals will be used to indicate like features used in describing to the preceding embodiment.

Figure 7:
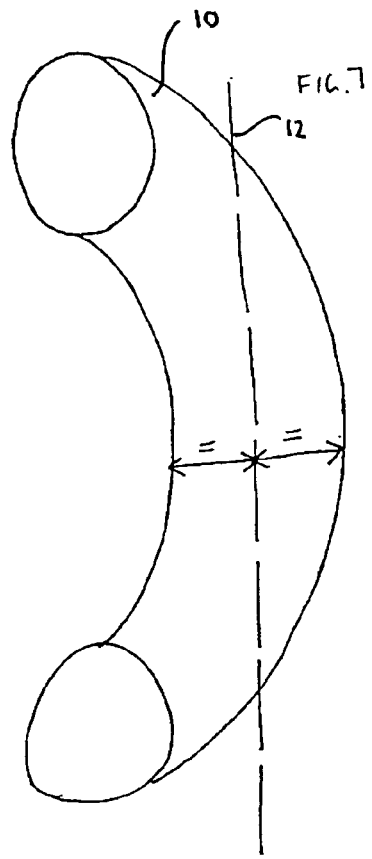
FIG. 7 is a schematic side view of an ascending aorta showing a resection line.

FIG. 7 is a schematic side view of a portion of ascending aorta 10. Line 12 is a resection line passing through the diameter of the midpoint cross section of the aorta 10 (see also FIG. 12).

Figure 8:
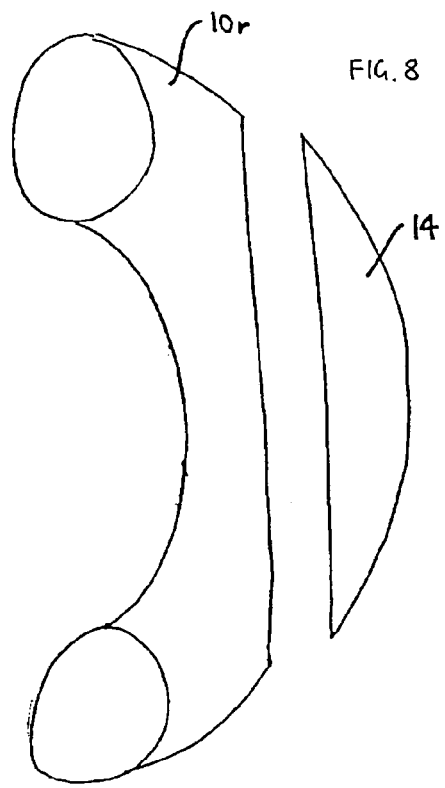
FIG. 8 is a schematic side view of the aorta shown in FIG. 7 after resection of a portion of the aorta.

FIG. 8 is a schematic view of the resected aorta 10r after cutting the aorta 10 along the resection line 12 and removal of a resected portion 14.

Figures 9, 10, 11:
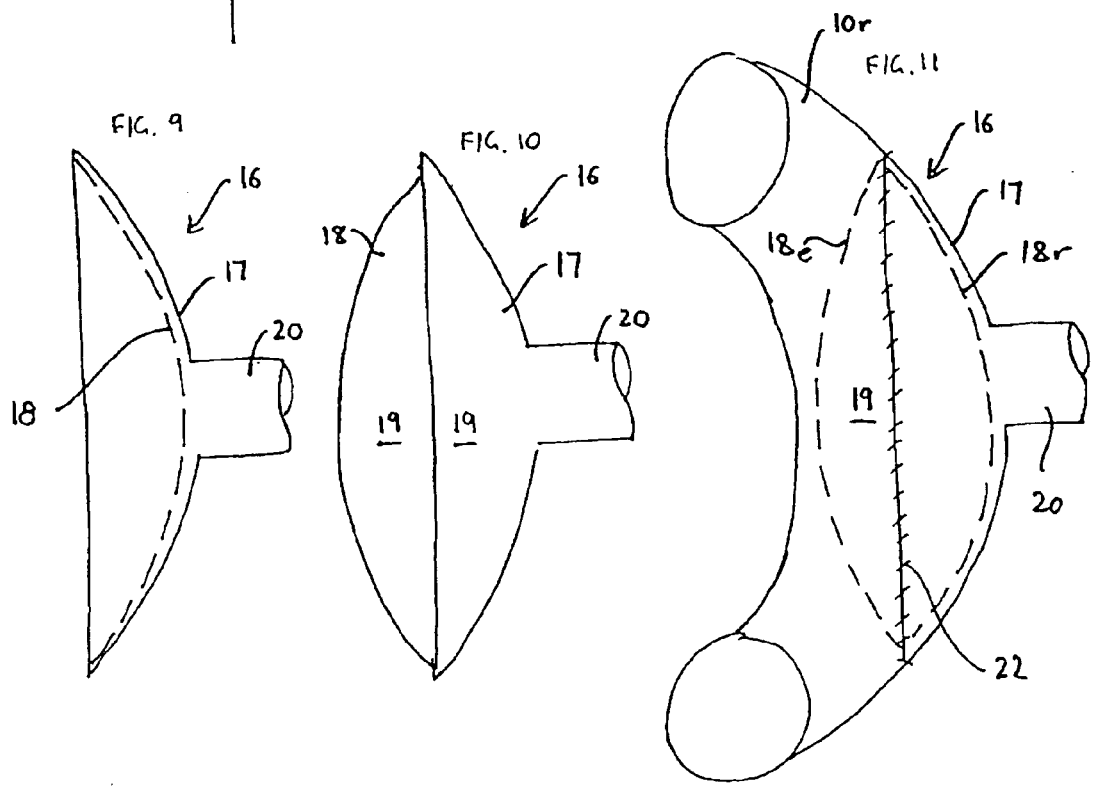
FIG. 9 is a schematic side view of another embodiment of a device for assisting the functioning of the heart with a withdrawn internal membrane.
FIG. 10 is a schematic side view of the device shown in FIG. 9 with an expanded membrane.
FIG. 11 is a schematic side view of the aorta shown in FIG. 8 after surgical attachment of the device shown in FIGS. 9 and 10 with the membrane shown in withdrawn and expanded positions.

FIG. 9 is a schematic side view of a heart assist device 16 in accordance with another embodiment of the invention. The device 16 has a relatively inelastic, preferably plastic, shell 17 and a flexible membrane 18 sealingly attached to the periphery of the shell 17. The membrane 18 defines an inflatable space 19 between it and the interior of the shell 17. The shell 17 also has an inlet/outlet port 20 which is adapted for connection to a motive means that can periodically introduce, and withdraw, a fluid (eg. a gas such as helium or a liquid such as a saline solution or an oil) to and from the space 19 in counter-pulsation with the patient's heart rhythm.

FIG. 9 illustrates the position of the membrane 18 relative to the shell 17 when fluid has been withdrawn from the space 19 and the membrane 18 has been retracted (18r in FIGS. 11 and 12). FIG. 10 illustrates the position of the membrane 18 relative to the shell 17 after fluid has been introduced into the space 19 and the membrane 18 has been expanded (18e in FIGS. 11 and 12). When the membrane 18 is expanded it is close to, but not abutting, the opposite interior wall of the aorta 10r.

The shell 17 has a peripheral edge of common shape to the opening formed in the aorta 10r after removal of the resected portion 14. This permits the device 16 to be attached to the resected aorta 10r by stitching between the periphery of the shell 17 and the periphery of the opening in the resected aorta 10r, as indicated by stitches 22 in FIG. 11.

Figure 5:
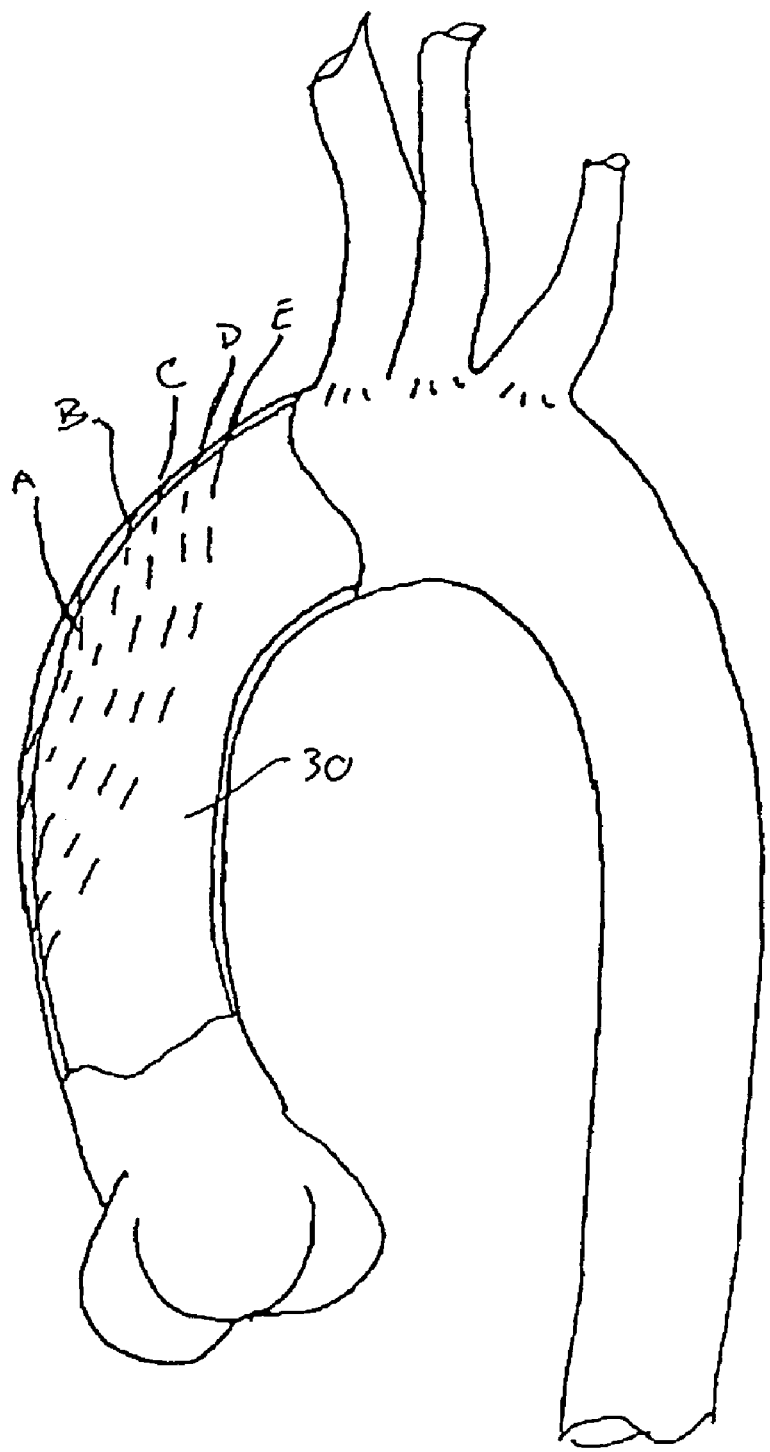
FIG. 5 is a part longitudinal cross-sectional view through the aorta of FIG. 3 along line 5-5 of FIG. 6, showing a sequence of shapes assumed by the aortic wall as it is deformed.
Figure 6:
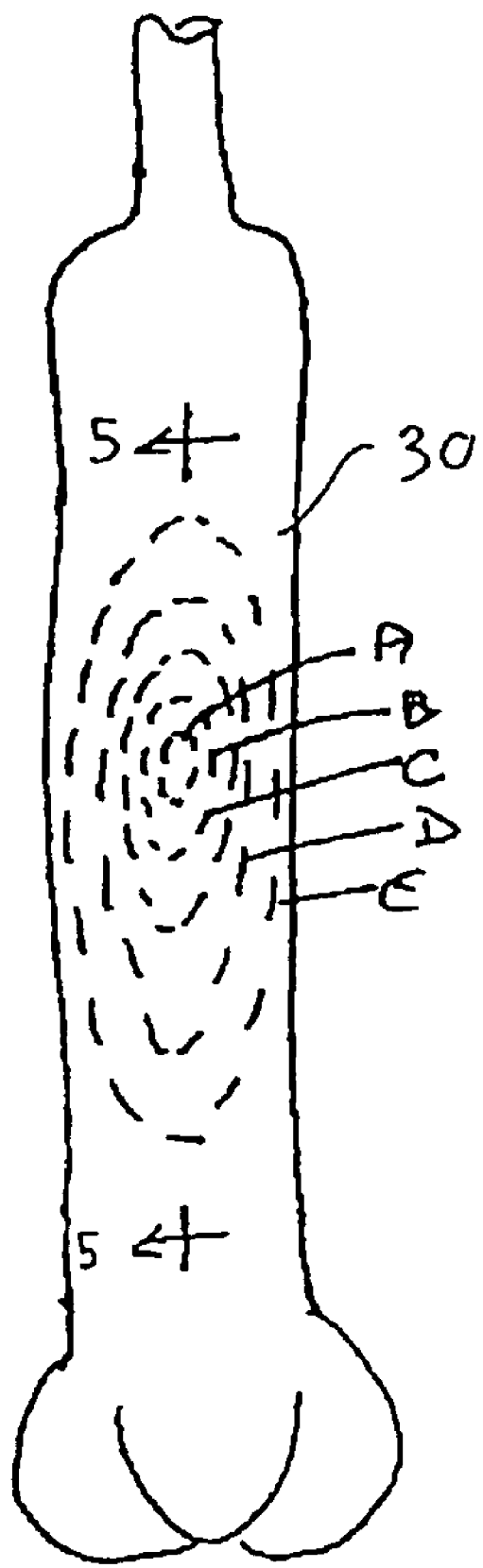
FIG. 6 is a lateral view from the right side of the aorta of FIG. 3, showing a sequence of lines of flexure as the aorta is deformed.

The motive means (not shown) include a fluid reservoir and a pump means adapted to pump the fluid from, the fluid reservoir to the port 20, and thus the space 19 between the interior of the shell 17 and the flexible membrane 18, and then withdrawn same, to expand (18e) and retract (18r) the membrane 18 as indicated in FIGS. 5 and 6. Suitable implantable fluid reservoirs and pump means are disclosed in the applicant's international PCT patent application Nos. PCT/AUO0/00654 and PCT/AU02/00974, which are hereby incorporated by cross reference.

More particularly, in use, the motive means is periodically actuated to introduce fluid into the space 19 in synchrony with the diastole period to reduce the interior volume of the aorta 10r and thereby provide additional pumping of the blood in the aorta 10r to assist the functioning of the heart. This introduction of fluid is alternated with periodic withdrawal of the fluid from the space 19 to allow the aorta 10r to return to its normal interior volume. As described above, the introduction of fluid expands the membrane 18 to be close to, but not abutting, the opposite interior wall of the aorta 10r. This maximises pumping volume without risk of the membrane 18 contacting and damaging the aorta 10r.

It will be appreciated that the heart assist device 16 includes a component, namely the membrane 18, which is blood contacting. However, the previously described disadvantages of blood contacting are minimised by the present invention as when the fluid is withdrawn from the space 19 the membrane 18 is drawn into a shape substantially replicating the original (now resected) aorta wall. As a result, no eddies or pockets are introduced into the blood flow path that may disrupt blood flow when the device 16 is not activated thereby substantially reducing clot risk.

Also, if the heart recovers the device 16 can be deactivated with the membrane 18 in the retracted position (see FIGS. 9 and 18r in FIGS. 11 and 12) allowing natural blood flow there through. In this connection, it should also be noted that heart assist devices have been proposed that function in parallel to the aorta and which receive the full diverted flow of blood originally intended for to the aorta. These devices can not be deactivated unlike the device according to the present invention.

Further, by installing the device 16 in a position vacated by the resected portion 14 of the aorta 10 it achieves a relatively high pumping volume for a relatively low device volume.

The flexible membrane 18 is preferably manufactured from a polyurethane or a polyurethane-polysiloxane block co-polymer material or other similar material, which encourages ingrowth of the passing blood cells and can eventually create a new "natural" cell lining.

The device according to the present invention is also particularly advantageous for use in patients whose aortas have become diseased as the device can be implanted in place of the resected damaged section.

A further embodiment of the device for assisting the functioning of a heart according to the present invention will now be described in relation to FIGS. 13 to 16. Like reference numerals will be used to indicate like features used in describing to the preceding embodiment. This embodiment is particularly suitable for use in patients having a naturally small aorta or an aorta that has shrunk through heart disease or the like.

FIG. 13 is a schematic cross sectional end view of a reduced diameter resected aorta 10r showing resection line 12 and resected portion 14. The periphery of the opening formed by removing the resected portion 14 is denoted 24 in FIG. 15. FIG. 14 shows the resected aorta 10r after its included angle α has been increased to α+ so as to open or stretch out the opening 24 in the aorta 10r. Such stretching allows the attachment of a heart assist device 16 of a similar size to that used in a healthy aorta. In this way, the effective cross section of the aorta available for pumping by the membrane 18 can be increased. For example, from about 707 mm$^2$ at an original diameter of 30 mm to about 1257 mm$^2$ at a stretched diameter of 40 mm. This results in a corresponding increase in the pumping volume of the aorta 10r.

FIG. 17 is a schematic side view of an ascending aorta 10 showing an alternatively positioned resection line 12. In this form, the resection line 12 is angled towards the top of the aorta 10 to resect the upper, radially outer arc of the aorta 10.

A further embodiment of a device for assisting the functioning of a heart according to the present invention will now be described in relation to FIG. 18. Like reference numerals will be used to indicate like features used in describing to the preceding embodiments.

Figure 18:
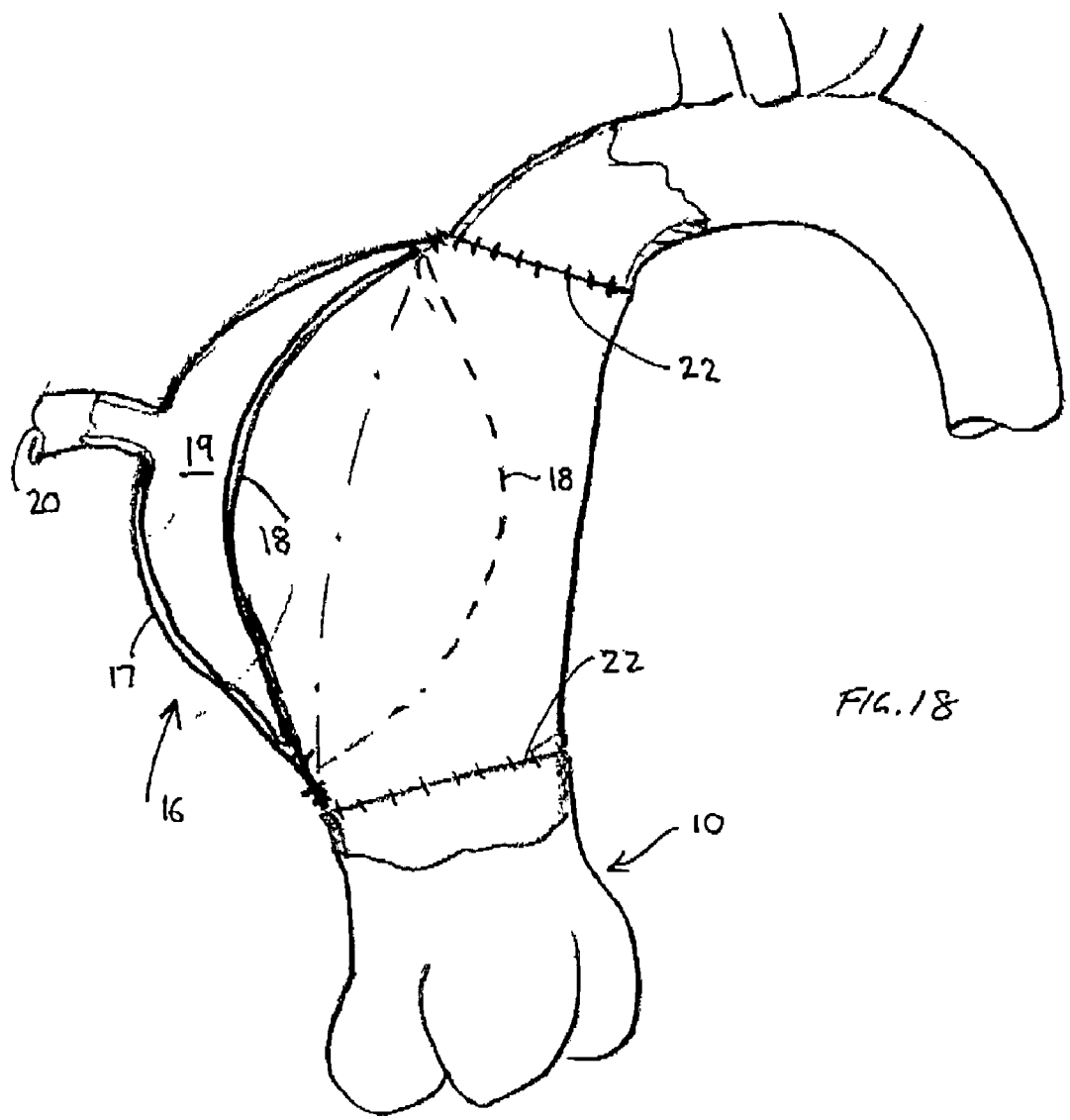
FIG. 18 is a cross sectional ventral view of the aorta of a patient with a further embodiment of a device for assisting the functioning of a heart.

In FIG. 18 the heart assist device is a patch device 16 attachable to the ends of the aorta 10, at stitches 22, formed by removing a length of the aorta. The patch device 10 is in the general shape of a truncated toroid with an externally facing hump that forms the inflatable space 19. The membrane 18 is attached to the patch device 16 about the periphery of the hump. The hump is disposed external to a line on the radially outer side, or passing through, the diameter of the mid point cross section of the aorta 10.

The flexible membrane 18 substantially replicates the shape of the interior of the hump when the fluid is withdrawn from the space 19. The membrane 18, when the fluid is introduced into the space 19, is expanded close to, but not abutting, the adjacent interior wall of the aorta, as is shown in phantom line.

Whilst the above embodiments have been described in relation to compressing the radially outer wall of the aorta, it would be appreciated by a person skilled in the art that other portions of the aorta can be deformed or other arteries can be deformed to assist in heart functions.

The heart assist devices described above are suitable for short and/or long term treatment for heart failure and/or myocardial ischemia.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. The method of providing counter-pulsation heart assist comprising:
installing a heart assist device on the ascending aorta of a patient, said heart assist device being capable of exerting compressive force on the outer wall of the aorta and extending around a portion of the circumference of the aorta; and
causing said heart assist device to cyclically compress a portion of the circumference of the aorta, such that the aorta is caused to flex along a continuous line which increases in length as the compressive force applied to the aorta increases.

2. The method of claim 1 wherein said heart assist device is a non-inflatable mechanical device.

3. The method of claim 2 wherein said mechanical device is rigid.

4. The method of claim 3 wherein said rigid device is adapted to move along a linear path or along an arcuate path.

5. The method of claim 4 wherein said rigid device moves at a right angle to the axis of the aorta if the portion of the artery contacted by the rigid device is straight or at a right angle to a tangent of a curved portion if the portion of the aorta contacted by the rigid device is curved.

6. The method of claim 1 wherein said heart assist device defines a membrane which in whole or in part comprises a chamber,
said chamber being capable of being inflated and deflated,
said chamber being configured such that when said chamber is deflated, the membrane is substantially smoothly curved, and
said membrane having a concave surface when it is deflated such that the concave surface faces inwardly toward the lumen of the aorta.

7. The method of claim 6 in which said membrane is substantially inelastic.

8. The method of claim 6 wherein said membrane is substantially elastic.

9. The method of claim 1 wherein the radially outer surface of the aorta is compressed.

10. The method of claim 1 wherein said aorta is compressed to create a curved ovate depression.

11. The method of claim 1 wherein said membrane is sealingly attached to a shell such that said chamber comprises the space between said shall and said membrane.

12. The method of claim 1 wherein the aorta is compressed through not more than 180 degrees of its circumference.

13. The method of claim 1 wherein said aorta is compressed through not more than 160 degrees of its circumference.

14. The method of claim 1 wherein said aorta is compressed through not more than 140 degrees of its circumference.

15. The method of claim 1 wherein said aorta is compressed through 100 to 140 degrees of its circumference.

16. The method of claim 1 wherein, when fully invaginated by said heart assist device, the invaginated portion of said wall is the mirror image of said wall when no compressive force is exerted.

17. The method of claim 1 wherein a layer of material is provided between said heart assist device and said wall.

18. The method of claim 1 wherein said aorta is compressed substantially without bunching or stretching.

19. The method of claim 1 wherein said compressive force causes said aorta to flex along a continuous line which increases in length as the pressure increases.

20. The method of claim 19 wherein said line has the shape of a conic section.

21. The method of claim 1 wherein said compressive force is exerted in a direction normal to a tangent of the radially outer surface of the longitudinal curve in the aorta.

22. The method of claim 21 wherein said compressive force causes said aorta to be progressively deformed along a line in a plane running through said aorta, which plane moves radially inwardly.

23. The method of claim 1 wherein access to the ascending aorta is achieved by a sternotomy.

24. The method of providing counter-pulsation heart assist comprising:
  installing inflatable heart assist device on the aorta of a patient,
  said heart assist device being capable of exerting compressive force on the outer wall of the aorta and extending around a portion of the circumference of the aorta,
  periodically introducing fluid to inflate said heart assist device in synchrony with the diastolic period of the heart to reduce the interior volume of the aorta, such that the aorta is caused to flex along a continuous line which increases in length as the compressive force applied to the aorta increases;
  deflating said heart assist device, and
  alternating periods of inflation with periods of deflation to periodically deflate the heart assist device in synchrony with the commencement of the systolic period of the heart, thereby allowing the portion of the aorta adjacent to said heart assist device to periodically return to normal interior volume.

25. The method of claim 24 wherein said heart assist device comprises a patch.

26. The method of claim 25 wherein said patch is provided with a flexible membrane sealingly attached to at least part of the interior of the patch thereby forming an inflatable space adjacent to the interior of the patch device which inflatable space is periodically inflated and deflated.

27. The method of claim 24 wherein said heart assist device comprises an inflatable member located adjacent to the outer wall of the aorta.

28. The method of providing counter-pulsation heart assist comprising:
  installing a heart assist device on the descending aorta of a patient,
  said heart assist device being capable of exerting compressive force on the outer wall of the aorta and extending around a portion of the circumference of the aorta;
  and causing said heart assist device to cyclically compress a portion of the circumference of the aorta, such that the aorta is caused to flex along a continuous line which increases in length as the compressive force applied to the aorta increases.

29. The method of claim 28 wherein said aorta is compressed to produce a smoothly curved circular depression.

30. The method of claim 28 wherein access to the descending aorta is achieved by a thoracotomy.

31. In a heart assist device which includes aorta deformation means to apply a counter-pulsation to an artery in the vasculature of a patient, characterized in that the deformation means applies a deforming force to the exterior of the artery such that the artery is caused to flex along a continuous line which increases in length as the counterpulsation pressure applied to the artery increases.

32. The device as claimed in claim 31, wherein the line has the shape of a conic section.

33. In a heart assist device which includes aorta deformation means to apply a counter-pulsation pressure to the ascending aorta of a patient, characterised in that the aorta deformation means applies a deforming force to the outside of the radially outer side of the curvature in the ascending aorta and that the aorta deformation means induces in the aorta a smoothly curved ovate depression as it moves to a position of maximum deformation of the aorta.

34. In a heart assist device which includes aorta deformation means to apply a counter-pulsation pressure to the descending aorta of a patient, characterised in that the aorta deformation means applies a deforming force to the outside of the descending aorta and that the aorta deformation means induces in the aorta a smoothly curved circular depression as it moves to a position of maximum deformation of the aorta.

35. In a heart assist device including artery deformation means adapted to periodically apply a deforming force to a curved artery in a direction substantially normal to a tangent to the radially outer surface of the longitudinal curve in the artery, the deforming force being such that the artery is progressively deformed along a line which lies in a plane running through the artery, the plane moving radially inwardly through the artery as the deformation increases.

36. In a counter-pulsation type heart assist device adapted for application to the outside of the wall of the ascending aorta of a patient, the device including an inflatable balloon extending around less than one half of the circumference of the aorta and means to inflate the balloon in counter-pulsation with the heart of a patient against which the device has been applied, the balloon having a substantially inelastic outer layer and an inner layer with a shape which is, when the balloon is deflated, smoothly curved and facing directly towards the lumen of the ascending aorta of the patient against which the device has been applied.

37. In a heart assist device adapted to apply a counter-pulsation force to the outside wall of at least the radially outer arc of the ascending aorta the force being applied to the radially outer arc of the aorta to cause the wall to invaginate, the device being characterised in that it includes deformation means for the application of the pressure to the wall which deformation means has, when the wall is fully invaginated, a shape which is substantially a mirror image of the section of the wall which has been invaginated before it was so invaginated.

38. The device as claimed in claim 37, wherein the deformation of the artery is induced by a balloon.

39. The device as claimed in claim 37, wherein the deformation of the artery is be induced by a rigid object.

40. The device as claimed in claim 37, wherein the deformation of the vessel does not extend around more than 180 degrees of the circumference of the vessel.

41. The device as claimed in claim 37, wherein the deformation of the vessel does not extend around more than 160 degrees of the circumference of the vessel.

42. The device as claimed in claim 37, wherein the deformation of the vessel does not extend around more than 140 degrees of the circumference of the vessel.

43. The device as claimed in claim 37, wherein the deformation of the vessel extends around between about 100 and about 140 degrees of the circumference of the vessel.

44. A method for improving cardiac performance in a subject, the method including the steps of:
  resecting a portion of the ascending aorta in the shape of a toroidal truncate and sealingly attaching the periphery of the device to the periphery of the opening in the aorta;
  implanting a device in accordance with any one of claims 31, 33, 34, 35, 36, or 37 fully within the thoracic cavity of a subject;
  actuating the motive means to periodically introduce the fluid into the space in synchrony with the diastolic period to reduce the interior volume of the aorta; and
  alternating the period of actuation with period of deactivation of the motive means to periodically withdraw the fluid from the space in synchrony with the commencement of the systolic period, thereby allowing the portion of the aorta adjacent the device to return to normal interior volume.

* * * * *